United States Patent
Green et al.

(10) Patent No.: US 6,833,406 B1
(45) Date of Patent: Dec. 21, 2004

(54) LIQUID DISPERSION POLYMER COMPOSITIONS, THEIR PREPARATION AND THEIR USE

(75) Inventors: Michael Green, Huddersfield (GB); Howard Roger Dungworth, Huddersfield (GB); Dwayne Erick Gavin, Hazel Crest, IL (US); Eleanor Bernice Ridley, Leeds (GB)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 0 days.

(21) Appl. No.: 10/432,761

(22) PCT Filed: Nov. 19, 2001

(86) PCT No.: PCT/EP01/13348
§ 371 (c)(1),
(2), (4) Date: May 28, 2003

(87) PCT Pub. No.: WO02/44228
PCT Pub. Date: Jun. 6, 2002

(30) Foreign Application Priority Data

Nov. 30, 2000 (GB) .............................................. 0029198

(51) Int. Cl.$^7$ .............................................. C08L 83/00
(52) U.S. Cl. .................... 524/588; 526/319; 526/303.1; 424/70.16
(58) Field of Search .......................... 524/588; 526/319, 526/303.1; 424/70.16

(56) References Cited

U.S. PATENT DOCUMENTS

| | | | |
|---|---|---|---|
| 4,072,805 A | * 2/1978 | Hrabak et al. ............... | 525/192 |
| 4,120,831 A | 10/1978 | Kuznetsova et al. .......... | 521/38 |
| 4,179,382 A | 12/1979 | Rudkin et al. ............... | 252/8.8 |
| 4,966,725 A | * 10/1990 | Singer et al. ............... | 252/8.63 |
| 5,039,642 A | 8/1991 | Chrobaczek et al. ......... | 502/155 |
| 5,189,102 A | 2/1993 | Tsubuko et al. ............. | 525/112 |
| 5,196,260 A | 3/1993 | Dirschl et al. .............. | 428/290 |
| 5,202,215 A | 4/1993 | Kanakura et al. ............ | 430/137 |
| 5,403,886 A | 4/1995 | Chrobaczek et al. ......... | 524/838 |
| 5,612,409 A | 3/1997 | Chrobaczek et al. ......... | 524/838 |
| 5,614,178 A | * 3/1997 | Bloom et al. ................ | 424/60 |
| 5,648,083 A | * 7/1997 | Blieszner et al. ........... | 424/402 |
| 6,165,446 A | * 12/2000 | Samain et al. ............... | 424/47 |
| 2002/0098212 A1 | * 7/2002 | Dupuis et al. ............... | 424/401 |

FOREIGN PATENT DOCUMENTS

| | | | |
|---|---|---|---|
| EP | 758 545 | * | 2/1997 |
| EP | 0758545 | | 2/1997 |
| GB | 871407 | | 6/1961 |
| GB | 2354765 | | 4/2001 |
| JP | 05-320683 | * | 12/1993 |
| WO | 99/08652 | * | 2/1999 |
| WO | 01/34681 | | 5/2001 |

OTHER PUBLICATIONS

International Cosmetic Ingredient Dictionary, Fifth Edition, vol. 1 (1993), pp. 573–574.

* cited by examiner

*Primary Examiner*—Kuo-Liang Peng
(74) *Attorney, Agent, or Firm*—Kevin T. Mansfield

(57) ABSTRACT

Liquid dispersion polymer compositions which comprise microparticles of a hydrophilic, water soluble or swellable polymer, preferably an acrylic-based polymer, dispersed in a silicone polymer fluid and an oil-in-water surfactant, are useful to prepare microparticulate thickening systems to thicken aqueous or aqueous/organic compositions, particularly for use in personal care and pharmaceutical formulations.

13 Claims, No Drawings

LIQUID DISPERSION POLYMER COMPOSITIONS, THEIR PREPARATION AND THEIR USE

FIELD OF THE INVENTION

The present invention relates to liquid dispersion polymer compositions which comprise a dispersed polymer phase, a continuous carrier phase and a surfactant, their preparation and the use of these liquid dispersion polymer compositions to prepare microparticulate thickening systems which thicken aqueous or aqueous/organic compositions. More particularly it relates to liquid dispersion polymer compositions which comprise microparticles of a hydrophilic, water soluble or swellable polymer, preferably an acrylic-based polymer, which is dispersed in a silicone polymer fluid carrier phase and an oil-in-water surfactant, their preparation and the use of these liquid dispersion polymer compositions to prepare microparticulate thickening systems to thicken aqueous or aqueous/organic compositions, particularly for use in personal care and pharmaceutical formulations.

Thickeners are used extensively in personal care formulations such as cosmetic and pharmaceutical formulations, to affect the aesthetics, product application and suspension and delivery of the active raw materials. Polymeric thickeners have been used for this purpose for many years. The types of polymeric thickeners that have been used range from natural gums such as guar, through modified natural materials such as hydroxyethyl cellulose, to synthetic thickeners such as the Carbomers® based on polyacrylic acids.

The Salcare® range of liquid dispersion polymers, available through Ciba Specialty Chemicals, is a range of microparticulate acrylic-based polymeric thickeners in a hydrophobic carrier medium. Salcare® SC91 is an anionic thickening agent based on a sodium acrylate polymer and mineral oil carrier with PPG-1 trideceth-6 as the activator surfactant. Salcare® SC92 is a cationic copolymer thickener and conditioner comprising polyquaternium 32 and mineral oil. Salcare® SC95 and Salcare® SC96 are cationic homopolymer thickeners and conditioners. Salcare® SC95 comprises polyquaternium 37 in mineral oil with PPG-1 trideceth-6. Salcare® SC96 comprises polyquaternium 37 in propylene glycol dicaprylate dicaprate with PPG-1 trideceth-6. Salcare AST is an anionic thickening agent based on a sodium acrylate polymer in soya bean oil with PPG-1 trideceth-6.

The tiny, spherical microparticles of the above hydrophilic acrylic polymers, whether anionic or cationic in charge, have a typical particle size in the range of 0.1–2 microns, with an average particle size in the range of 0.5–1.0 microns. The polymer microparticles are preferably manufactured by methods in which water soluble vinyl addition monomers are polymerized utilizing a water-in-oil polymerization route.

On stirring of any of the above liquid dispersion polymers into an aqueous system, the activator surfactant converts the hydrophobic carrier into an oil-in-water emulsion. By the term "activator surfactant" is meant a surfactant which activates the conversion of the hydrophobic carrier into an oil-in-water emulsion. At the same time the hydrophilic polymer expands on exposure to water but does not dissolve, resulting in a smooth and rapid viscosity increase. Typically the polymer particles swell to give a microparticulate thickening system comprising polymer particles having a typical particle size in the range of 2.5–5 microns in diameter. Since the water molecules move into the small polymer particles by osmosis, the osmotic effect experienced by the polymer particle is a balance between water and any electrolyte present in the system. Hence high electrolyte levels reduce the swelling of the polymer particles.

The microparticulate thickening systems have a pseudoplastic rheological profile which gives good stability and suspension characteristics at low shear rates (such as those experienced by the product on standing), and low apparent viscosity's at high shear rates, which corresponds to excellent rub-in characteristics.

As previously mentioned, the continuous organic carrier phase for the above Salcare® liquid dispersion polymers is provided at least in part by a silicone polymer fluid.

SUMMARY OF THE INVENTION

In one aspect the present invention provides a liquid dispersion polymer composition comprising a hydrophilic, water soluble or swellable polymer as a dispersed polymer phase, a silicone polymer fluid as a continuous carrier phase and an oil-in-water surfactant, wherein the polymer is in the form of microparticles having an average particle size in the range of 0.1 to 2 microns.

Typically the liquid dispersion polymer composition comprises
a) from 35% to 65% by weight of the polymer,
b) from 20% to 50% by weight of a silicone polymer fluid, and
c) from 5% to 25% by weight of a surfactant or a surfactant mixture, each based on the total weight of the composition.

Advantageously the hydrophilic polymer a) is water swellable, i.e. it is sufficiently cross-linked to swell but not dissolve in water. Preferably it is acrylic-based. Also it is preferably anionic or cationic.

The silicone polymer fluids b) are well known to the cosmetic industry and have been used for many years in hair and skin formulations. They are particularly favored over mineral oils for their improved aesthetic feel on skin and hair and also for the sheen they impart when employed in hair care applications. The products of the instant invention provide a compatibility across the different ionic systems and give a level of formulation versatility using silicone technology that is not provided by any other liquid dispersion polymer.

Preferably the surfactant mixture c) comprises both surfactants useful in the manufacture of the microparticles of swellable polymer a), and at least one surfactant which serves as the activator for the subsequent oil-in-water microparticulate thickening emulsions. This activator surfactant for the oil-in-water thickening emulsions comprises from 1.0% to 10.0% by weight of the composition, preferably from 2.0% to 8.0% by weight of the composition. Preferably the activator surfactant is a nonionic oil-in-water emulsifier having a HLB generally above 7. Suitable emulsifiers of this type are well known to those skilled in the art. Ethoxylated alcohols are preferred.

Additionally the composition may contain minor amounts of other components which do not affect its essential characteristics. Typically these other components may include up to about 3% by weight each of water and volatile organic solvents as well as small amounts of other components which are left over from the preparation of the water soluble or swellable polymers.

Advantageously the composition comprises
a) from 40% to 60% by weight of the polymer, wherein the polymer is anionic or cationic and is water swellable, b) from 25% to 45% by weight of a silicone polymer fluid, and
c) from 8% to 20% by weight of a surfactant or a surfactant mixture, each based on the total weight of the composition.

A particularly preferred composition comprises
a) from 45% to 58% by weight of the polymer, wherein the polymer is anionic or cationic and is water swellable,
b) from 30% to 40% by weight of a silicone polymer fluid, and
c) from 10% to 18% by weight of a mixture of surfactants, each based on the total weight of the composition.

A very particularly preferred composition comprises
a) from 45% to 58% by weight of the water swellable polymer, wherein the polymer is cationic,
b) from 32% to 38% by weight of a silicone polymer fluid,
c) from 12% to 18% by weight of a mixture of surfactants, each based on the total weight of the composition.

Still another aspect of the present invention is the provision of thickened aqueous or water-containing compositions, in particular personal care formulations, which comprise
a) 0.1% to 8% by weight, preferably 1% to 6% by weight of a liquid dispersion polymer composition as described above,
b) 0.1% to 70%, preferably 2% to 35% by weight of additional ingredients, for example personal care ingredients such as cosmetic or pharmaceutical excipients and/or active ingredients and
c) 45% to 99% of water or a mixture of water and a water-miscible organic solvent such as a lower alcohol.

Such lower alcohols include ethanol, isopropyl alcohol, propylene glycol, di-isopropyl alcohol and other known lower alcohols.

These compositions may be in the form of lotions, creams, salves, gels, milks, sprays, foams or ointments.

The additional components can be any ingredient which may form part of a thickened aqueous emulsion of the oil-in-water type. Non-limiting examples of cosmetic ingredients include: antimicrobials (such as triclosan "RTM", farnesol "RTM"); skin conditioning agents and emollients such as lanolin and derivatives thereof; esters such as iso-propyl propanoate, decyl oleate, isopropyl isostearate, trioctanoin, triisostearin, myristyl propionate; fatty alochols; squalene; silicones such as cyclomethicone, dimethicone, dimethicone copolyol; acetamide monoethanolamine; dimethyl polysiloxane; moisturizers such as aloe vera, barrier creams, emollients, alpha and beta hydroxy acids such as lacti acid and glycolic acid; anti-inflammatory actives like allantoin and bisabolol; UV sun screening agents such as para aminobenzoic acid, octyl salicylate, and octyl methoxycinnamate, "sunless" tanning agents, whitening agents, insect repellents, essential oils such as patchouli oil, peppermint oil, rosemary oil, citronella oil, tea tree oil, orange or lemon oils, cedarwood oil and sandalwood oil, vitamins, colours and pigments; hair conditioners such as amodlmethicone, cyclomethicone, panthenol, lauramide diethanolamine, lauramine oxide and silk protein; perfume components; hair dyes and bleaches and preservatives such as methyl-, ethyl-, propyl-paraben and imidazolidinyl urea.

Pharmaceutically active ingredients may vary widely and include all therapeutic agents intended for topical application to the skin or hair, in particular substances to treat itching, tingling, scaling, inflammation or infection of the skin, burns, and scalp hair loss of humans or other mammals.

Still another aspect of the present invention is the provision of a method for the preparation of a therapeutic lotion, cream, salve, gel or ointment which comprises mixing 0.1% to 8% by weight, preferably 1% to 6% by weight of a liquid dispersion polymer as described above into an aqueous or aqueous/organic composition which contains from 0.1% to 70% by weight of at least one therapeutic agent and/or excipient.

Still another aspect of the present invention is the provision of a method for the topical treatment of the skin, which comprises applying a composition as defined above to the skin, face or scalp of a human being or other mammal in need of such treatment. The type of treatment will depend on the active ingredient(s) dissolved or suspended in the composition. For example the composition may comprise facial creams such as barrier cream, a moisturizer cream, lotion or milk, a cleanser or toner, a hand and body milk or lotion, a body spray, creams, lotions or milks containing sun-screens against UV-A and UV-B radiation, a "sunless" tanning cream, lotion or spray, a skin bleaching cream, lotion or spray, a depilatory cream, a hair conditioning cream, lotion or shampoo, a hair dyeing cream or lotion, a pre- or aftershave cream, lotion, gel or balm, a disinfectant cream, lotion, ointment or gel, a soothing cream, lotion or spray as an after sun application for sunburn, etc.

Other aspects of the present invention will become apparent from the following discussion and the examples. The examples merely illustrate certain aspects of the invention and are not intended to be limiting thereof.

DETAILED DESCRIPTION OF THE INVENTION

The hydrophilic, water swellable acrylic-based liquid dispersion polymer compositions employed in the present invention may be either anionic or cationic. Said polymers may be homopolymers or copolymers. They are formed from one or more monoethylenically unsaturated monomers that are either water soluble anionic or cationic monomers or from a predominantly anionic or cationic blend of monomers that may consist of anionic and cationic monomers or may consist of a mixture of anionic and/or cationic monomers and a minor amount of nonionic monomers.

The polymers may conveniently be obtained in the form of microparticles having an average particle size in the range of 0.1–2 microns by reverse phase emulsion polymerization of suitable monomers in a hydrophobic liquid, i.e. a liquid which has sufficiently low miscibility with water that it can be used as the non-aqueous phase in a reverse phase polymerization. The liquid must have substantially no solvating effect for the polymer, or for the monomers from which it is formed, throughout the range of temperatures at which the polymer is likely to be synthesized (for instance from 15 to 100° C.), since a solvating medium would be unsatisfactory for reverse phase emulsion polymerization. Likewise, the monomer or monomer blend must be water soluble to enable reverse phase polymerization to be carried out.

Suitable anionic monomers include acrylic acid, methacrylic acid and their alkali metal and ammonium salts, 2-acrylamido-2-methyl-propanesulfonic acid and its salts, sodium styrene sulfonate and the like. Acrylic acid is the most preferred anionic monomer. Preferably the carboxylic acid groups are at least 50%, advantageously 65–85% in the form of an alkali metal salt or ammonium salt, especially the sodium salt.

Suitable cationic monomers include diallyl dialkyl monomers such as diallyl dimethyl ammonium chloride, but preferably the cationic monomer is a dialkylaminoalkyl (meth)acrylate or -acrylamide. Although the polymer can be in free base form, especially when it is a cationic acrylamide or methacrylamide, it is preferably in the form of an acid addition or quaternary ammonium salt, such as (meth) acrylamido propyltrimethyl ammonium chloride.

When the monomer is a cationic acrylamide or methacrylamide, the dialkylaminoalkyl group is generally a dialkylamino propyl or dialkylamino isopropyl group. When the monomer is a cationic acrylate or methacrylate, the dialkylaminoalkyl group is generally a dialkylaminoethyl group.

It is usually preferred for the cationic monomer to be a dialkylaminoalkyl(meth)acrylate acid salt or quaternary ammonium salt, most preferably dimethylaminoethyl methacrylate. Usually it is present as the methyl chloride quaternary ammonium salt.

Suitable nonionic monomers include acrylamide, methacrylamide, N,-dialkylacrylamides, N,N,-dialkylacrylamides, N-vinyl pyrrolidone and water soluble hydroxy-substituted acrylic or methacrylic esters.

If a cationic blend is used, the amount of cationic monomer is preferably more than 50% by weight of the blend, and usually it is at least 70% or at least 80% by weight of the blend. The preferred cationic polymers are formed wholly from cationic monomers.

If an anionic blend is used, the amount of anionic monomer is preferably more than 60% by weight of the blend, and usually it is at least 80% by weight of the blend. The preferred anionic polymers are formed wholly from anionic monomers.

The liquid dispersion polymer compositions are advantageously crosslinked by incorporating a small amount of a suitable crosslinking agent such as a polyfunctional vinyl addition monomer into the polymerization mixture. Preferably a water soluble crosslinking agent is used.

Any of the conventional ethylenically unsaturated cross linking agents or poly ethylenically unsaturated cross linking agents which are soluble in the monomer or monomer blend can be used, including materials which are di-, tri- or tetraethylenically unsaturated. Preferred are diethylenically unsaturated compounds such as methylene bis acrylamide, ethylene glycol di(meth)acrylate, di(meth)acrylamide, triallyl ammonium salts, vinyloxyethylacrylate or -methacrylate and the like. Methylene bis acrylamide is the most preferred crosslinking agent.

The amount of cross linking agent is generally in the range from 100 to 10,000 parts by weight of cross linking agent per million parts (by dry weight) of monomer. Most preferably it is around 500 to 2000 ppm, especially 500 to 900 ppm for either cationic or anionic monomers. Optimum amounts can be determined by routine experimentation.

Especially preferred polymers for use in the present invention are the anionic polymer dispersed in Salcare® SC91 and Salcare® AST, and the cationic polymers dispersed in Salcare® SC92, Salcare® SC95 and Salcare® SC96 liquid dispersion polymers.

The hydrophilic polymers are prepared by reverse phase emulsion polymerization of hydrophilic monomers, preferably one or more acrylate and/or methacrylate monomers, in a hydrophobic liquid phase. Reverse phase emulsion polymerization is a well known technique which is described for example in U.S. Pat. No. 4,628,078, the disclosure of which is incorporated by reference in its entirety.

The continuous phase for the preparation of the instant liquid dispersion polymer compositions is provided at least in part by a silicone polymer fluid. Since the liquid dispersion polymer compositions are primarily intended for cosmetic or pharmaceutical purposes, silicone polymer fluids which are cosmetically and/or pharmaceutically acceptable and which are sufficiently hydrophobic to be useful as the continuous phase in a reverse phase polymerization are preferably used as the continuous phase. Many such materials are known and are commercially available. Such silicone polymer fluids include cyclomethicones, dimethicones, phenyl dimethicones, phenyl trimethicones and the like, including mixtures thereof. Phenyl trimethicones are preferred.

The amount of the hydrophobic liquid phase used in the polymerization is dictated primarily by the need to provide a satisfactory reverse phase emulsion medium. This would generally be at least about 0.5 parts by weight of the silicone polymer fluid per part by weight of the hydrophilic polymer (dry weight). In order to obtain liquid dispersion polymer compositions having higher amounts of the microparticles in the silicone polymer fluid, for example from 1.2 to about 1.7 parts by weight of the hydrophilic polymer (dry weight) in the silicone polymer fluid, as well as to facilitate processing, it is expedient to employ a volatile inert hydrophobic solvent. Suitable inert hydrophobic solvents include hydrocarbons and halogenated hydrocarbons. One particularly preferred hydrocarbon mixture is Isopar G "RTM" from Exxon. Conveniently 1 to 2 parts, preferably 1.3 to 1.9 parts of the volatile inert hydrophobic solvent per part of the hydrophilic polymer on a dry weight basis is employed.

The polymer is prepared by conventional reverse phase emulsion procedures, namely by adding 1 part by weight (dry weight) of at least one aqueous ethylenically unsaturated monomer, optionally including a sequesterant and a crosslinking ethylenically unsaturated monomer, into about 1 to 3 parts by weight of a hydrophobic liquid comprising at least in part a liquid hydrophobic silicone polymer fluid and containing about 0.1 to 0.2 parts of at least one conventional water-in-oil emulsifier having a HLB value below 9.0 and optionally 0.5 to 10.0 parts of a polymeric stabilizer surfactant, with intensive agitation so as to form a substantially stable emulsion of the required fine particle size. Suitable water-in-oil emulsifiers are well known to those skilled in the art. Sorbitan esters are preferred. Diethylenetriamine pentaacetic acid, sodium salt is a suitable sequesterant. The ethylenically unsaturated monomer may be diethylenically or polyethylenically unsaturated.

The reaction mixture is purged with nitrogen and polymerization is initiated by addition of a conventional source of free radicals. Suitable polymerization initiators are well known to those skilled in the art. Typical free radical-forming catalysts include peroxygen compounds such as sodium, potassium and ammonium persulfates, caprylyl peroxide, benzoyl peroxide, hydrogen peroxide, pelargonyl peroxide, cumene hydroperoxide, tertiary butyl diperphthalate, tertiary butyl perbenzoate, sodium peracetate, di(2-ethylhexyl)peroxydicarbonate, and the like, as well as azo catalysts such as azodiisobutyronitrile. Other useful catalysts are the heavy metal-activated catalyst systems. A preferred type of polymerization initiator is a redox initiation pair. After initiation appropriate temperature and agitation conditions are maintained until the conversion of the monomer to polymer is substantially complete. Appropriate conditions are well known to those of ordinary skill in the art.

The water and any volatile solvent are then removed from the reverse phase emulsion, for example by distillation under reduced pressure, so as to produce a substantially anhydrous stable dispersion of polymer particles less than 2 microns in size dispersed in the silicone polymer fluid.

About 1.0% to 10.0% by weight, based on the weight of the composition, preferably from 2% to 8% by weight of a nonionic oil-in-water emulsifier having a HLB generally above 7 is added after distillation is complete. Suitable emulsifiers of this type are well known to those skilled in the art. Ethoxylated alcohols are preferred.

It is a further feature of the invention that a suitable polymeric stabiliser surfactant is employed as a processing aid to maintain emulsion integrity through the distillation process and to provide for the final liquid polymer dispersion to be a free flowing liquid, even when it contains high levels of microparticles of the water soluble or swellable dispersed polymer.

Advantageously 0.5 to 10.0 parts, preferably 1.0 to 6.0 parts, of this surfactant is employed per part by weight (dry weight) of the ethylenically unsaturated monomer.

A preferred polymeric surfactant is a copolymer of an alkyl(meth)acrylate and an amino functional monomer, which may be prepared as follows:

Alkyl(meth)acrylate, amino functional monomer and a suitable oil soluble thermal initiator, for example 2,2'-Azobis(2-methylbutyronitrile), are dissolved in an inert solvent, for example an aliphatic or aromatic hydrocarbon solvent such as isopar G "RTM". This mixture is fed into a vessel containing further solvent and thermal initiator over a period of 2 to 6 hours at reaction temperatures of 80 to 90° C. The reaction is maintained at this temperature for a further two hours before being cooled and run off.

The alkyl group of the Alkyl(meth)acrylate may be any suitable alkyl group, however $C_8$ to $C_{22}$ groups are preferred.

The amino functional monomer is of the general formula (1):

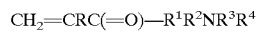

$$CH_2=CRC(=O)-R^1R^2NR^3R^4 \qquad (1)$$

R is hydrogen or $C_1$ to $C_4$ alkyl
$R^1$ is oxygen or nitrogen
$R^2$ is $C_1$ to $C_4$ alkyl
$R^3$ is hydrogen or $C_1$ to $C_{10}$ alkyl
$R^4$ is $C_1$ to $C_{10}$ alkyl The alkyl(meth)acrylate:amino functional monomer ratio may be between 0.5 to 8.0:1 on a molar basis. Preferably between 0.75 to 6.0:1, and most preferably between 1.0 to 4.0:1 on a molar basis.

The molecular weight may be determined by conventional chromatography techniques well known to those skilled in the art. Typical molecular weights may be in the range of 10,000 to 60,000, most typically in the range of 15,000 to 40,000.

Upon stirring the liquid dispersion into an aqueous system, the non-ionic surfactant converts the hydrophobic carrier into an oil-in-water emulsion. At the same time the hydrophilic polymer expands on exposure to water resulting in a smooth and rapid viscosity increase. Typically the polymer particles swell to give a microparticulate thickening system comprising polymer particles having a typical particle size in the range of 2.5 to 5.0 microns.

The inventive liquid dispersion compositions provide microparticulate thickening systems which give effective thickening to aqueous or aqueous/organic formulations at concentrations of 0.1 to 8.0%. Preferably 1% to 6% by weight. In addition however they combine the thickening effect of the liquid dispersion polymer with the advantages of the silicone polymer fluid.

The liquid dispersion polymer compositions are compatible with a wide variety of personal care active ingredients and auxiliaries. Typical formulation examples where the polymers may be used include:

Skin Care formulations including all kind of face end body emulsions like creams, lotions, milks and sprays for caring, cleansing, deodorisation and depilation, colour cosmetics such as; liquid foundations, liquid eyeshadows, liquid blushers, lipsticks and aqueous mascara's; facial masks, lip balms, skin care formulations like body washes, all kind of shaving products; hand soaps, soap bars and soap liquids.

Hair Care formulations which include; hair conditioners, hair colourations (permanent, semi-permanent and temporary), styling gels, lotions and creams, shampoos, hair relaxers, hair perms and hair masks.

Sun Tan formulations such as: sun tan creams, lotions and sprays, sun blocks, tan accelerators, after sun creams, lotions and sprays and sunless tanning lotions or creams.

The formulation examples below merely illustrate a few representative aspects of the formulating possibilities and are not intended to be limiting in any way. The most particularly preferred composition is where the polymer in the liquid dispersion polymer comprises microparticles of a water swellable cationic polymer, and wherein the silicone polymer fluid is a phenyl trimethicone.

All percents are percent by weight of the formulation. Viscosity's are determined with a Brookfield viscometer.

EXAMPLE 1

Daily Use Hair Conditioning Moisturising Lotion/Cream

| Trade Name | Supplier | INCI Name | % |
|---|---|---|---|
| 1 | | Aqua | to 100 |
| 2 Salcare ® Silicone | Ciba Specialty Chemicals | To be determined | 2.75 |
| 3 Sorbitol | UPI | Sorbitol | 1.50 |
| 4 Eldew CL 301 | Ajinomoto | Cholesteryl/Behenyl/ Octyldodecyl/ Lauroyl Glutamate | 0.50 |
| 5 Cupl PIC | Bernel | PPG-2 Isocetech-20 Acetate | 0.25 |
| 6 Panthenol-Liquid | Roche | Panthenol (Pro-Vitamin B5) | 0.25 |
| 7 Nipaguard BPX | Nipa | Phenoxyethanol & Methyl & Propyl-paraben & 2-Bromo-2-Nitropropane 1-3-Diol | 0.15 |
| 8 Fragrance | | if required | |

Method

1) Add 1 to a beaker, initiate agitation then add 3, 4 and 5 mixing well for approximately 5 to 10 minutes. Then add 6, 7 and 8 with increased mixing.
2) After increasing stirrer speed add 2 slowly, continuing to stir slowly for about 5 to 10 minutes until viscous and homogeneous.

| Typical Properties: | |
|---|---|
| Appearance: | smooth low viscosity cream |
| Viscosity: | 10,000–20,000 cPs |
| pH: | 3.5–4.25. |

EXAMPLE 2

General Daily Use Hand and Body Lotion

|   | Trade Name | Supplier | INCI Name | % |
|---|---|---|---|---|
| 1 |  |  | Aqua | to 100 |
| 2 | Glycerin | Procter & Gamble | Glycerin | 3.0 |
| 3 | Kessco | Stepan Company | Octyl Isononanoate | 5.5 |
| 4 | Aloe Vera | Active Organics | Aloe Barbadensis | 0.5 |
| 5 | Salcare ® Silicone | Ciba Specialty Chemicals | To be determined | 2.5 |
| 6 | Crodamol OPG | Croda | Octyl Pelargonate | 2.25 |
| 7 | Germaben li | Sutton | Propylene Glycol & Diazolindinyl Urea & Methyl Paraben & Propyl Paraben as desired | 0.75 |
| 8 | Fragrance |  | if required |  |

Method

1) Add 1 to a beaker, initiate agitation then add 2, 3 and 4 mixing well for approximately 5 to 10 minutes. Then add 6, 7 and 8 with increased mixing.
2) After increasing stirrer speed add 5 slowly, continuing to stir slowly for about 5 to 10 minutes until viscous and homogeneous.

Typical Properties

| Appearance: | "rich" lotion |
|---|---|
| Viscosity: | 7,500–10,500 cPs |
| pH: | 5.5–7.0. |

EXAMPLE 3

After Sun Lotion/Cream

|   | Trade Name | Supplier | INCI Name | % |
|---|---|---|---|---|
| 1 |  |  | Aqua | to 100 |
| 2 | Sweet Almond Oil | AE Connock | Prunus Dulcis | 4.50 |
| 3 | Actiphyte Kola Nut | Active Organics | Kola Nut Extract | 5.00 |
| 4 | Aloe Vera | Active Organics | Aloe Barbadenis | 2.00 |
| 5 | Salcare ® Silicone | Ciba Specialty Chemicals | To be determined | 3.25 |
| 6 | Tinoderm P | Ciba Specialty Chemicals | Aqua & Panthenol & Caprylic/Capric Triglyceride & polysorbate 80 & Lecithin | 1.25 |
| 7 | Nipaguard BPX | Nipa Laboratories | Phenoxethanol & Methyl & Propyl-paraben & 2-Bromo-2-Nitropropane-1,3-Diol | 0.20 |

Method

1) Add 1 to a beaker, initiate agitation then add 2, 3, 4, 6 and 7 mixing well for approximately 5 to 10 minutes.
2) After increasing stirrer speed add 5 slowly, continuing to stir slowly for about 5 to 10 minutes until viscous and homogeneous.

Typical Properties

| Appearance: | flowable lotion |
|---|---|
| Viscosity: | 5,000–8,000 cPs |
| pH: | 5.0–6.5. |

What is claimed is:

1. A liquid dispersion polymer composition comprising a hydrophilic, water soluble or swellable polymer which is dispersed in a silicone polymer fluid and an oil-in-water surfactant, wherein the polymer is in the form of microparticles having an average particle size in the range of 0.1 to 2 microns, which liquid dispersion polymer composition comprises
   a) from 40% to 60% by weight of the polymer,
   b) from 25% to 45% by weight of the silicone polymer fluid and
   c) from 8% to 20% by weight of the surfactant or surfactant mixture, each based on the total weight of the composition.

2. A liquid dispersion polymer composition according to claim 1, wherein the polymer is anionic or cationic and is water swellable.

3. A liquid dispersion polymer composition according to claim 1, wherein the polymer is polyquaternium 37 which is crosslinked with 500 to 2000 ppm of a crosslinking agent.

4. A liquid dispersion polymer composition according to claim 1, wherein the hydrophilic polymer is prepared by reverse phase emulsion polymerization of one or more acrylate and/or methacrylate monomers in a hydrophobic liquid phase which comprises at least one silicone polymer fluid.

5. A liquid dispersion polymer composition according to claim 1, wherein the silicone polymer fluid is cosmetically and/or pharmaceutically acceptable.

6. A thickened aqueous or water-containing composition, which comprises
   a) 0.1% to 8% by weight of a liquid dispersion polymer composition according to claim 1,
   b) 0.1% to 70% by weight of additional ingredients, and
   c) 45% to 99% of water or a mixture of water and a water-miscible organic solvent.

7. A thickened aqueous or water-containing composition according to claim 6, which is in the form of a lotion, cream, salve, gel, ointment, milk, spray or foam.

8. A method for the preparation of a therapeutic lotion, cream, salve, gel, ointment milk, spray or foam which comprises mixing 0.1% to 8% by weight of a liquid dispersion polymer according to claim 1 into an aqueous or aqueous/organic composition which contains from 0.1% to 70% by weight of at least one therapeutic agent and/or excipient.

9. A method for the therapeutic topical treatment of the skin, which comprises applying a composition as defined in claim 6 to the skin, face, scalp or hair of a human being or other mammal in need of such treatment.

10. A method for the preparation of a liquid dispersion polymer composition according to claim 1, which comprises carrying out a reverse phase emulsion polymerization of a hydrophilic ethylenically unsaturated monomer in a hydrophobic liquid phase which comprises at least one silicone polymer fluid.

11. A method according to claim 10, which comprises
    a) adding 1 part by weight (dry weight) of a hydrophilic ethylenically unsaturated monomer, optionally including a sequesterant and a crosslinking ethylenically unsaturated monomer, into about 1 to 3 parts by weight of a hydrophobic liquid comprising a liquid hydrophobic silicone and, optionally, a volatile inert hydrophobic solvent and containing at least one water-in-oil emulsifier having a HLB value below 9.0 and optionally a polymeric stabilizer surfactant, with intensive agitation so as to form a substantially stable emulsion of fine particle size, b) providing an inert atmosphere, c) adding a free radical initiator, d) maintaining appropriate temperature and agitation conditions until the conversion of the monomer to polymer is substantially complete, e) removing water and the optional volatile solvent from the reverse phase emulsion under reduced pressure, so as to produce a substantially anhydrous stable dispersion of polymer particles less than 2 microns in size dispersed in the silicone, and f) adding from 0.5% to 8% by weight, based on the weight of the composition, of a nonionic oil-in-water emulsifier having a HLB above 7 to the dispersion of the polymer particles in the silicone.

12. A method according to claim 10, wherein the hydrophilic ethylenically unsaturated monomer is a dimethylaminoethyl methacrylate quaternised with methyl chloride, the crosslinking ethylenically unsaturated monomer is methylene bis acrylamide, the silicone polymer fluid is a phenyl trimethicone, and a polymeric stabilizer surfactant is present.

13. A method according to claim 11, wherein the polymeric stabilizer surfactant is a reaction product of an alkyl (meth)acrylate and an amino functional monomer.

* * * * *